United States Patent [19]

Hagedorn

[11] 4,128,651
[45] Dec. 5, 1978

[54] BIS-QUATERNARY PYRIDINIUM-2-ALDOXIME SALTS AND A PROCESS FOR THEIR PREPARATION

[75] Inventor: Ilse Hagedorn, Freiburg, Fed. Rep. of Germany

[73] Assignee: Merck Patent Gesellschaft mit beschrankter Haftung, Darmstadt, Fed. Rep. of Germany

[21] Appl. No.: 786,693

[22] Filed: Apr. 11, 1977

[30] Foreign Application Priority Data

Apr. 14, 1976 [DE] Fed. Rep. of Germany ....... 2616481

[51] Int. Cl.² .................. A61K 31/44; A61K 31/455; C07D 213/78
[52] U.S. Cl. ..................................... 424/263; 424/266; 544/331; 544/296; 546/262; 546/263
[58] Field of Search ....... 260/296 D, 295 R, 295 AM, 260/295.5 A, 296 M; 424/266, 263

[56] References Cited

U.S. PATENT DOCUMENTS 3,773,775 11/1973 Hagedorn .......................... 260/296

*Primary Examiner*—Alan L. Rotman
*Attorney, Agent, or Firm*—Millen & White

[57] ABSTRACT

Bis-quaternary pyridinium-2-aldoxime salts of the formula

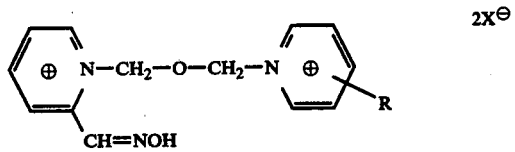

wherein R is $-CO-R^1$, $-CO-NR^2R^3$ or $-COOR^4$; $R^1$ is alkyl of 1 – 6 carbon atoms, cyclohexyl, Ar or benzyl; $R^2$ is H, alkyl of 1 – 6 carbon atoms, cyclohexyl, Ar, aralkyl of 7 – 13 carbon atoms or 2-pyrimidyl; $R^3$ is alkyl of 2 – 6 carbon atoms, cyclohexyl, Ar, aralkyl of 7 – 13 carbon atoms or 2-pyrimidyl; $R^4$ is alkyl of 2 – 6 carbon atoms, cyclohexyl, Ar or benzyl; Ar is phenyl or phenyl monosubstituted or polysubstituted by alkyl of 1 – 4 carbon atoms, methoxy, Cl, or naphthyl and X is Cl, Br or I, are antidotes for phosphorus-containing pesticides and chemical warfare agents.

17 Claims, No Drawings

BIS-QUATERNARY PYRIDINIUM-2-ALDOXIME SALTS AND A PROCESS FOR THEIR PREPARATION

BACKGROUND OF THE INVENTION

This invention relates to novel antidotes for poisoning by phosphorus-containing cholinesterase inhibitors.

SUMMARY OF THE INVENTION

In a compositional aspect, this invention relates to a bis-quaternary pyridinium-2-aldoxime salt of Formula I

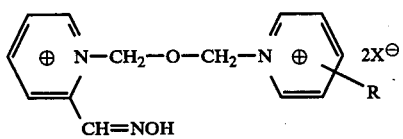

wherein R is $-CO-R^1$, $-CO-NR^2R^3$ or $-COOR^4$; $R^1$ is alkyl of 1–6 carbon atoms, cyclohexyl, Ar or benzyl; $R^2$ is H, alkyl of 1–6 carbon atoms, cyclohexyl, Ar, aralkyl of 7–13 carbon atoms or 2-pyrimidyl; $R^3$ is alkyl of 2–6 carbon atoms, cyclohexyl, Ar, aralkyl of 7–13 carbon atoms or 2-pyrimidyl; $R^4$ is alkyl of 2–6 carbon atoms, cyclohexyl, Ar or benzyl; Ar is phenyl, naphthyl or phenyl substituted by up to 5 of alkyl of 1–4 carbon atoms, methoxy or Cl; and X is Cl, Br or I.

In another compositional aspect, this invention relates to a pharmaceutical composition, comprising a compound of Formula I, in admixture with a pharmaceutically acceptable carrier.

In a preparative aspect this invention relates to a process for preparing a pyridinium-2-aldoxime salt of Formula I, by reacting a 1-X-methoxymethyl-2-hydroxyiminomethylpyridinium halide wherein X is as above with a pyridine compound of Formula II

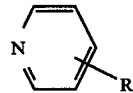

wherein R is as above.

In a method-of-use aspect, this invention relates to a prophylactic or therapeutic method of treating a person or animal for intoxication with a phosphorus-containing cholinesterase inhibitor, comprising administering to the person or animal a compound of Formula I in an amount effective as an antidote for the cholinesterase inhibitor and in admixture with a pharmaceutically-acceptable carrier.

DETAILED DESCRIPTION

In Formula I, R is most preferably in the 3-position, and is secondarily preferred in the 4-position, of the pyridine ring. R can also be in the 2-position.

In $R^1$ and Ar, "alkyl" is preferably methyl, ethyl or tert.-butyl, as well as n-propyl, isopropyl, n-butyl, isobutyl or sec.-butyl. In $R^3$ and $R^4$, "alkyl" is preferably tert.-butyl or ethyl, n-propyl, isopropyl, n-butyl, isobutyl, sec.-butyl, 1-, 2-, or 3-pentyl, 2-methyl-1-butyl, isopentyl (3-methyl-1-butyl), tert.-pentyl (2-methyl-2-butyl), 3-methyl-2-butyl, neopentyl (2,2-dimethyl-1-propyl), 1-, 2- or 3-hexyl, 2-methyl-1-, -2-, or -3-pentyl, 3-methyl-1-, -2- or -3-pentyl, 4-methyl-1- or -2-pentyl, 2-ethyl-1-butyl, 2,3-dimethyl-1- or -2-butyl, 2,2-dimethyl-1-butyl, 3,3-dimethyl-1-butyl or pinacolyl (3,3-dimethyl-2-butyl).

Ar is preferably phenyl, 1-naphthyl or 2-naphthyl. If Ar is substituted phenyl, the substitution is preferably monosubstitution or di-substitution. In the case of polysubstituted aryl, the substituents are preferably identical. Accordingly, Ar is preferably o-, m- or p-tolyl; o-, m-, or p-ethylphenyl; o-, m- or p-n-propylphenyl; o-, m- or p-isopropylphenyl; o-, m- or p-n-butylphenyl; o-, m-, or p-isobutylphenyl; o-, m- or p-sec.-butylphenyl; o-, m- or p-tert-butylphenyl; o-, m- or p-methoxyphenyl; o-, m- or p-chlorophenyl; 2,3-, 2,4-, 2,5-, 2,6-, 3,4- or 3,5-dimethylphenyl or 2,3-, 2,4-, 2,5-, 2,6-, 3,4- or 3,5-dichlorophenyl. Ar can also be phenyl substituted by up to five substituents, for example, dimethoxyphenyl, such as 3,4-dimethoxyphenyl; trimethoxyphenyl, such as 3,4,5-trimethoxy-phenyl; pentamethylphenyl; pentachlorophenyl or 2,6-dimethyl-4-tert.-butylphenyl.

Aralkyl is preferably benzyl; o-, m- or p-alkylbenzyl, wherein alkyl is of 1–4 carbon atoms, most preferably, tert.-butyl; 1-phenylethyl or 2-phenylethyl; 1-, 2- or 3-phenylpropyl, 1-, 2-, 3- or 4-phenylbutyl or diphenylmethyl.

Other examples of preferred $R^1$ are phenyl or cyclohexyl, $R^2$ is preferably H, and $R^3$ and $R^4$ are preferably alkyl of 2–6 carbon atoms, most preferably tert.-butyl.

Preferred compounds of Formula I are all those in which at least one of the substituents is as indicated above. Some exemplary preferred groups of compounds of Formula I are those wherein:

(Ia) R is in the 3- or 4-position and is $-CO-R^1$;
(Ib) R is in the 3- or 4-position and is $-CO-NR^2R^3$;
(Ic) R is in the 3- or 4-position and is $-COOR^4$;
(Id) R is in the 3- or 4-position and is $-COR^1$ and $R^1$ is alkyl of 1–4 carbon atoms, cyclohexyl, phenyl, alkylphenyl of 1–4 carbon atoms in the alkyl, methoxyphenyl, dichlorophenyl or benzyl;
(Ie) R is in the 3- or 4-position and is $-CO-NR^2R^3$ and $R^3$ is alkyl of 2–6 carbon atoms, cyclohexyl, phenyl, alkylphenyl of 1–4 carbon atoms in the alkyl, dichlorophenyl, benzyl, alkylbenzyl of 1–4 carbon atoms in the alkyl, or diphenylmethyl;
(If) R is in the 3- or 4-position and is $-COOR^4$ and $R^4$ is alkyl of 2–6 carbon atoms, cyclohexyl, phenyl, naphthyl or benzyl;
(Ig) R is in the 3-position;
(Ih) R is in the 3-position and is $-COC_6H_5$;
(Ii) R is in the 3-position and is $-CONHR^3$ and $R^3$ is tert.-butyl or phenyl;
(Ij) R is in the 3-position and is $-COOR^4$ and $R^4$ is alkyl of 2–4 carbon atoms;
(Ik) R is in the 3-position and is $-CO$-cyclohexyl;
(Il) R is in the 3-position and is $-CONH$-tert.-butyl; and
(Im) R is in the 3-position and is $-COO$-tert.-butyl.

Other compounds are those of Formula I wherein:
(In) R is in the 2-position, and is $-COR^1$;
(Io) R is in the 2-position and is $-CONR^2R^3$;
(Ip) R is in the 2-position and is $-COOR^4$;
(Iq) $R^1$ is alkyl of 1–6 carbon atoms, including each of (Ia) and (In);
(Ir) $R^1$ is 2-pyrimidyl, including each of (Ia) and (In);
(Is) $R^2$ is H, including each of (Ib), (Ie) and (Io);
(It) $R^2$ is alkyl of 1–6 carbon atoms including each of (Ib), (Ie) and (Io);

(Iu) $R^2$ is cyclohexyl, including each of (Ib), (Ie) and (Io);

(Iv) $R^2$ is Ar or aralkyl of 7-13 carbon atoms, including each of (Ib), (Ie) and (Io);

(Iw) $R^2$ is 2-pyrimidyl, including each of (Ib), (Ie) and (Io);

(Ix) $R^3$ is aralkyl of 8-13 carbon atoms, including each of (Ib) and (Io);

(Iy) $R^3$ is 2-pyrimidyl including each of (Ib) and (Io);

(Iz) $R^4$ is substituted phenyl, including each of (Ic) and (Ip);

(Iaa) X is Cl, including each of (Ia)–(Iz);

(Ibb) X is Br, including each of (Ia)–(Iz) and (Icc) X is I, including each of (Ia)–(Iz).

The preparation of compounds of Formula I is carried out according to methods described in the literature, for example, DOS No. 1,670,672, under reaction conditions which are known as suitable for the reaction.

The starting material used is preferably 1-chloromethoxymethyl-2-hydroxyiminomethyl-pyridinium chloride (compare DOS No. 1,670,672), which is known and which can, if desired, be converted in situ to the corresponding iodine derivative by reaction with sodium iodide.

The synthesis according to the invention is preferably carried out in an inert, preferably aprotic, solvent, for example a ketone, such as acetone or butanone; a nitrile, such as acetonitrile; a halogenated hydrocarbon, such as chloroform; a sulfoxide, such as dimethylsulfoxide; or an amide, such as dimethylformamide. Mixtures of these solvents with one another are also suitable. The preferred reaction temperatures are between 0° and 60°, but the reaction is preferably carried out at room temperature (15°–30°).

It is also possible to convert a resulting salt of Formula I to another salt. Thus, for example, a resulting iodide (X is I) can be dissolved in hot water and treated with an excess of silver chloride or silver bromide with vigorous stirring, as with a turbine and heating for one to two hours. After the precipitate has been filtered off, the filtrate is concentrated and crystallization is induced by adding a solvent, for example, ethanol.

The reaction products are generally salts which crystallize well, which are sparingly soluble in the reaction media and which can be isolated merely by filtration. If desired, they can be recrystallized, for example, from water.

Pyridinium salts of Formula I possess valuable pharmacological properties and are well tolerated. They are outstandingly suitable for combating symptoms of poisoning caused by plant protection agents or chemical warfare agents which contain phosphorus. Whether administered prophylactically or therapeutically, they are outstandingly effective against poisoning caused by Soman and other cholinesterase inhibitors. These antidote effects can be detected, for example, on mice, by the procedure of H. Oldiges and K. Schoene, *Arch, Toxikol.*, Volume 26, pages 293-305 (1970).

The compounds can, therefore, be used as medicaments in human and veterinary medicine. They can also be used as intermediate products for the preparation of further medicaments.

Compounds of Formula I can be used for the production of pharmaceutical preparations by conversion into a suitable dosage form, together with at least one excipient or auxiliary and optionally together with one or more further active compounds. The formulations thus obtained can be employed as medicaments in human or veterinary medicine.

Excipients are organic or inorganic substances which are suitable for parenteral, oral or rectal administration or topical application and which do not react with the new compounds. Examples include water, benzyl alcohol, polyethylene glycols, gelatin, carbohydrates, such as lactose or starch, magnesium stearate, talc and petroleum jelly.

Solutions, preferably aqueous solutions, and suspensions, emulsions or implants are used for parenteral administration. Tablets, dragees, capsules, syrups, elixirs or drops are used for oral administration. Suppositories are used for rectal administration and ointments, creams or powders for topical application.

The compounds can also be lyophilized and the resulting lyophilizates can be used for the production of injectable preparations. The indicated formulations can contain auxiliaries, such as lubricants, preservatives, stabilizers and/or wetting agents, emulsifiers, salts for affecting the osmotic pressure, buffer substances and one or more additional active compounds.

The substances of the invention are generally administered analogously to known, commercially available antidotes, for example, Obidoxime. See U.S. Pat. No. 3,137,702. Preferred dosages are between about 10 and 2,000 mg., most preferably between 200 and 1,000 mg. per dosage unit, if desired, with the prior protective administration of 2–5 mg. (per dosage unit) of atropine intravenously or intramuscularly. The dosage of a compound of Formula I is preferably between about 0.2 and 40 mg./kg. of body weight.

The specific dose for a particular patient depends, however, on diverse factors, for example, the activity of the specific compound employed, the age, body weight and general state of health, the time of administration and the time and severity of the particular poisoning to which the therapy is being used as antidote. Parenteral administration is preferred, whether for prophylaxis or therapeutically, that is, before or after intoxication with a cholinesterase inhibitor.

Each of the compounds of Formula I given in the examples which follow is particularly suitable for the preparation of pharmaceutical formulations.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

All the melting points in the following text involve decomposition.

EXAMPLE 1

2.4 g. of 1-chloromethoxymethyl-2-hydroxyiminomethylpyridinium chloride and 1.9 g. of 3-benzoylpyridine are added to a solution of 6 g. of dry sodium iodide in 100 ml. of absolute acetone. The mixture is stirred for 4 hours at room temperature with exclusion of moisture and is filtered. The resulting 3-benzoylpyridinium-1-methyl 2-hydroxyiminomethylpyridinium-1-methyl ether diiodide is washed with acetone and recrystallized from water. M.p. 156°–158°.

EXAMPLES 2 to 57

The following are obtained analogously to Example 1, using: 3-acetylpyridine, 4-acetylpyridine, 3-trimethylacetylpyridine, 4-trimethylacetylpyridine, 3-cyclohexylcarbonylpyridine, 4-cyclohexylcarbonylpyridine, 2-benzoylpyridine, 4-benzoylpyridine, 3-o-toluylpyridine, 4-o-toluylpyridine, 3-m-toluylpyridine, 4-m-toluylpyridine, 3-p-toluylpyridine, 4-p-toluylpyridine, 3-p-tert.-butylbenzoylpyridine, 4-p-tert.-butylbenzoylpyridine, 3-p-methoxybenzoylpyridine, 4-p-methoxybenzoylpyridine, 3-(3,4-dichlorobenzoyl)pyridine, 4-(3,4-dichlorobenzoyl)pyridine, 3-phenylacetylpyridine, 4-phenylacetylpyridine, nicotinic acid N-ethylamide, nicotinic acid N-tert.-butylamide, isonicotinic acid N-tert.-butylamide, nicotinic acid N-pinacolylamide, nicotinic acid N-cyclohexylamide, nicotinic acid anilide, isonicotinic acid anilide, nicotinic acid p-tert.-butylanilide, nicotinic acid 3,4-dichloroanilide, nicotinic acid N-benzylamide, nicotinic acid N-(p-tert.-butylbenzyl)amide, nicotinic acid N-(diphenylmethyl)-amide, nicotinic acid N-(2-pyrimidyl)amide, nicotinic acid N-methyl-N-tert.-butylamide, nicotinic acid N-methylanilide, nicotinic acid ethyl ester, isonicotinic acid ethyl ester, nicotinic acid n-propyl ester, isonicotinic acid n-propyl ester, nicotinic acid isopropyl ester, isonicotinic acid isopropyl ester, nicotinic acid n-butyl ester, isonicotinic acid n-butyl ester, nicotinic acid isobutyl ester, isonicotinic acid isobutyl ester, nicotinic acid sec.-butyl ester, isonicotinic acid sec.-butyl ester, nicotinic acid tert.-butyl ester, isonicotinic acid tert.-butyl ester, nicotinic acid pinacolyl ester, nicotinic acid cyclohexyl ester, nicotinic acid phenyl ester, nicotinic acid 2-naphthyl ester and nicotinic acid benzyl ester:

2. 3-Acetylpyridinium-1-methyl 2-hydroxyiminomethylpyridinium-1-methyl ether diiodide, m.p. 158°–160°.
3. 4-Acetylpyridinium-1-methyl 2-hydroxyiminomethylpyridinium-1-methyl ether diiodide.
4. 3-Trimethylacetylpyridinium-1-methyl 2-hydroxyiminomethylpyridinium-1-methyl ether diiodide, m.p. 152°–154°.
5. 4-Trimethylacetylpyridinium-1-methyl 2-hydroxyiminomethylpyridinium-1-methyl ether diiodide.
6. 3-Cyclohexylcarbonylpyridinium-1-methyl 2-hydroxyiminomethylpyridinium-1-methyl ether diiodide, m.p. 146°–148°.
7. 4-Cyclohexylcarbonylpyridinium-1-methyl 2-hydroxyiminomethylpyridinium-1-methyl ether diiodide.
8. 2-Benzoylpyridinium-1-methyl 2-hydroxyiminomethylpyridinium-1-methyl ether diiodide.
9. 4-Benzoylpyridinium-1-methyl 2-hydroxyiminomethylpyridinium-1-methyl ether diiodide, m.p. 153°–155°.
10. 3-o-Toluylpyridinium-1-methyl 2-hydroxyiminomethylpyridinium-1-methyl ether diiodide.
11. 4-o-Toluylpyridinium-1-methyl 2-hydroxyiminomethylpyridinium-1-methyl ether diiodide.
12. 3-m-Toluylpyridinium-1-methyl 2-hydroxyiminomethylpyridinium-1-methyl ether diiodide.
13. 4-m-Toluylpyridinium-1-methyl 2-hydroxyiminomethylpyridinium-1-methyl ether diiodide.
14. 3-p-Toluylpyridinium-1-methyl 2-hydroxyiminomethylpyridinium-1-methyl ether diiodide, m.p. 145°–147°.
15. 4-p-Toluylpyridinium-1-methyl 2-hydroxyiminomethylpyridinium-1-methyl ether diiodide.
16. 3-p-tert.-Butylbenzoylpyridinium-1-methyl 2-hydroxyiminomethylpyridinium-1-methyl ether diiodide, m.p. 147°–149°.
17. 4-p-tert.-Butylbenzoylpyridinium-1-methyl 2-hydroxyiminomethylpyridinium-1-methyl ether diiodide.
18. 3-p-Methoxybenzoylpyridinium-1-methyl 2-hydroxyiminomethylpyridinium-1-methyl ether diiodide, m.p. 125°–127°.
19. 4-p-Methoxybenzoylpyridinium-1-methyl 2-hydroxyiminomethylpyridinium-1-methyl ether diiodide.
20. 3-(3,4-Dichlorobenzoyl)pyridinium-1-methyl 2-hydroxyiminomethylpyridinium-1-methyl ether diiodide.
21. 4-(3,4-Dichlorobenzoyl)pyridinium-1-methyl 2-hydroxyiminomethylpyridinium-1-methyl ether diiodide.
22. 3-Phenylacetylpyridinium-1-methyl 2-hydroxyiminomethylpyridinium-1-methyl ether diiodide.
23. 4-Phenylacetylpyridinium-1-methyl 2-hydroxyiminomethylpyridinium-1-methyl ether diiodide, m.p. 130°–132°.
24. 3-N-Ethylcarbamoylpyridinium-1-methyl 2-hydroxyiminomethylpyridinium-1-methyl ether diiodide, m.p. 135°–137°.
25. 3-N-tert.-Butylcarbamoylpyridinium-1-methyl 2-hydroxyiminomethylpyridinium-1-methyl ether diiodide monohydrate, m.p. 119°–121°.
26. 4-N-tert.-Butylcarbamoylpyridinium-1-methyl 2-hydroxyiminomethylpyridinium-1-methyl ether diiodide monohydrate, m.p. 129°–131°.
27. 3-N-Pinacolylcarbamoylpyridinium-1-methyl 2-hydroxyiminomethylpyridinium-1-methyl ether diiodide, m.p. 158°–160°.
28. 3-N-Cyclohexylcarbamoylpyridinium-1-methyl 2-hydroxyiminomethylpyridinium-1-methyl ether diiodide, m.p. 172°–174°.
29. 3-N-Phenylcarbamoylpyridinium-1-methyl 2-hydroxyiminomethylpyridinium-1-methyl ether diiodide, m.p. 155°–157°.
30. 4-N-Phenylcarbamoylpyridinium-1-methyl 2-hydroxyiminomethylpyridinium-1-methyl ether diiodide.
31. 3-N-p-tert.-Butylphenylcarbamoylpyridinium-1-methyl 2-hydroxyiminomethylpyridinium-1-methyl ether diiodide, m.p. 140°–142°.
32. 3-N-(3,4-Dichlorophenyl)carbamoylpyridinium-1-methyl 2-hydroxyiminomethylpyridinium-1-methyl ether diiodide monohydrate, m.p. 124°–126°.
33. 3-N-Benzylcarbamoylpyridinium-1-methyl 2-hydroxyiminomethylpyridinium-1-methyl ether diiodide, m.p. 186°–188°.
34. 3-N-p-tert.-Butylbenzylcarbamoylpyridinium-1-methyl 2-hydroxyiminomethylpyridinium-1-methyl ether diiodide, m.p. 123°–125°.
35. 3-N-Diphenylmethylcarbamoylpyridinium-1-methyl 2-hydroxyiminomethylpyridinium-1-methyl ether diiodide, m.p. 127°–129°.
36. 3-N-(2-Pyrimidyl)carbamoylpyridinium-1-methyl 2-hydroxyiminomethylpyridinium-1-methyl ether diiodide, m.p. 172°–174°.
37. 3-N-Methyl-N-tert.-butylcarbamoylpyridinium-1-methyl 2-hydroxyiminomethylpyridinium-1-methyl ether diiodide, m.p. 160°–162°.
38. 3-N-Methyl-N-phenylcarbamoylpyridinium-1-methyl 2-hydroxyiminomethylpyridinium-1- methyl ether diiodide sesquihydrate, m.p. 115°–117°.
39. 3-Ethoxycarbonylpyridinium-1-methyl 2-hydroxyiminomethylpyridinium-1-methyl ether diiodide, m.p. 151°–153°.
40. 4-Ethoxycarbonylpyridinium-1-methyl 2-hydroxyiminomethylpyridinium-1-methyl ether diiodide.
41. 3-n-Propoxycarbonylpyridinium-1-methyl 2-hydroxyiminomethylpyridinium-1-methyl ether diiodide, m.p. 129°–131°.
42. 4-n-Propoxycarbonylpyridinium-1-methyl 2-hydroxyiminomethylpyridinium-1-methyl ether diiodide.
43. 3-Isopropoxycarbonylpyridinium-1-methyl 2-hydroxyiminomethylpyridinium-1-methyl ether diiodide, m.p. 147°–149°.
44. 4-Isopropoxycarbonylpyridinium-1-methyl 2-hydroxyiminomethylpyridinium-1-methyl ether diiodide.
45. 3-n-Butoxycarbonylpyridinium-1-methyl 2-hydroxyiminomethylpyridinium-1-methyl ether diiodide, m.p. 127°–129°.
46. 4-n-Butoxycarbonylpyridinium-1-methyl 2-hydroxyiminomethylpyridinium-1-methyl ether diiodide.
47. 3-Isobutyoxycarbonylpyridinium-1-methyl 2-hydroxyiminomethylpyridinium-1-methyl ether diiodide.
48. 4-Isobutoxycarbonylpyridinium-1-methyl 2-hydroxyiminomethylpyridinium-1-methyl ether diiodide.
49. 3-sec.-Butoxycarbonylpyridinium-1-methyl 2-hydroxyiminomethylpyridinium-1-methyl ether diiodide.
50. 4-sec.-Butoxycarbonylpyridinium-1-methyl 2-hydroxyiminomethylpyridinium-1-methyl ether diiodide.
51. 3-tert.-Butoxycarbonylpyridinium-1-methyl 2-hydroxyiminomethylpyridinium-1-methyl ether diiodide, m.p. 132°–134°.
52. 4-tert.-Butoxycarbonylpyridinium-1-methyl 2-hydroxyiminomethylpyridinium-1-methyl ether diiodide.
53. 3-Pinacolyloxycarbonylpyridinium-1-methyl 2-hydroxyiminomethylpyridinium-1-methyl ether diiodide, m.p. 152°–154°.
54. 3-Cyclohexyloxycarbonylpyridinium-1-methyl 2-hydroxyiminomethylpyridinium-1-methyl ether diiodide, m.p. 142°–144°.
55. 3-Phenoxycarbonylpyridinium-1-methyl 2-hydroxyiminomethylpyridinium-1-methyl ether diiodide, m.p. 143°–145°.
56. 3-(2-Naphthoxycarbonyl)pyridinium-1-methyl 2-hydroxyiminomethylpyridinium-1-methyl ether diiodide, m.p. 117°–119°.
57. 3-Benzyloxycarbonylpyridinium-1-methyl 2-hydroxyiminomethylpyridinium-1-methyl ether diiodide, m.p. 145°–147°.

EXAMPLE 58

6 g. of 3-benzoylpyridinium-1-methyl 2-hydroxyiminomethylpyridinium-1-methyl ether diiodide are dissolved in 600 ml. of hot water. 9 g. of silver chloride are added and the mixture is stirred for 2 hours at 60°.
The mixture is filtered while hot and the filtrate is evaporated. 3-Benzoylpyridinium-1-methyl 2-hydroxyiminomethylpyridinium-1-methyl ether dichloride is obtained from the residue by treatment with ethanol, in the form of the monoethanolate hemihydrate, m.p. from 78° (with decomposition).

The dichlorides corresponding to the diiodides of Example 1 are obtained analogously, for example, 3-N-tert.-butylcarbamoylpyridinium-1-methyl 2-hydroxyiminomethylpyridinium-1-methyl ether dichloride monohydrate, m.p. 116°–118°.

The corresponding dibromides are obtained analogously using silver bromide, e.g., 3-benzoylpyridinium-1-methyl 2-hydroxyiminomethylpyridinium-1-methyl ether dibromide, m.p. 116°–118°.

EXAMPLES 59 AND 60

As in Example 1, there are obtained from 3-isobutyroylpyridine and 3-p-chlorobenzoylpyridine, respectively:
59. 3-Isobutyroylpyridinium-1-methyl 2-hydroxyiminomethylpyridinium-1-methyl ether diiodide, m.p. 142°–144°.
60. 3-p-Chlorobenzoylpyridinium-1-methyl 2-hydroxyiminomethylpyridinium-1-methyl ether diiodide, m.p. 152°–154°.

The example which follows relates to a pharmaceutical formulation which contains a compound of Formula I:

EXAMPLE A: AMPOULES

A solution of 1 kg. of 3-benzoylpyridinium-1-methyl 2-hydroxyiminomethylpyridinium-1-methyl ether dichloride in 10 l. of water is made up and is filtered under sterile conditions and charged into ampoules in such a way that each ampoule contains 1,000 mg. of active compound.

Ampoules which contain one or more of the remaining active compounds of Formula I can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:
1. A bis-quaternary pyridinium-2-aldoxime salt of the formula

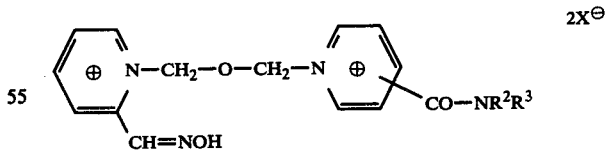

wherein $R^2$ is H, cyclohexyl, Ar, aralkyl of 7–13 carbon atoms; $R^3$ is alkyl of 2–6 carbon atoms, cyclohexyl, Ar or aralkyl of 7–13 carbon atoms; Ar is phenyl, naphthyl or phenyl substituted by up to 5 of alkyl of 1–4 carbon atoms, methoxy or Cl; and X is Cl, Br or I.
2. A compound of claim 1 wherein $R^2$ is H and $R^3$ is tert.butyl, cyclohexyl, phenyl, ethyl, p-tert.-butylphenyl, p-tert.-butylbenzyl, 3,4-dichlorophenyl or benzyl.
3. A bis-quaternary pyridinium-2-aldoxime salt of the formula

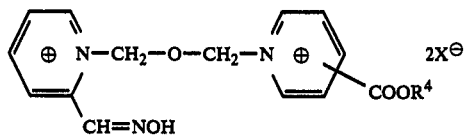

wherein R[4] is n-propyl, n-butyl, t-butyl, cyclohexyl, Ar or benzyl; Ar is phenyl, naphthyl or phenyl substituted by up to 5 of alkyl of 1–4 carbon atoms, methoxy or Cl; and X is Cl, Br or I.

4. A compound of claim 3 wherein COOR[4] is in the 3- or 4-position.

5. A compound of claim 4 wherein —COOR[4] is in the 3-position and R[4] is cyclohexyl.

6. A bis-quaternary pyridinium-2-aldoxime salt of the formula

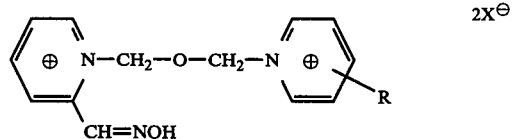

wherein R is —CO-R[1]; R[1] is alkyl of 1–6 carbon atoms, cyclohexyl, Ar or benzyl; Ar is phenyl, naphthyl or phenyl substituted by up to 5 of alkyl of 1–4 carbon atoms, methoxy or Cl; and X is Cl, Br or I.

7. 3-Benzoylpyridinium-1-methyl 2-hydroxyiminomethylpyridinium-1-methyl ether dichloride, dibromide or diiodide, a compound of claim 6.

8. 3-tert.-Butoxycarbonylpyridinium-1-methyl 2-hydroxyiminomethylpyridinium-1-methyl ether dichloride, dibromide or diiodide, a compound of claim 3.

9. 3-N-tert.-Butylcarbamoylpyridinium-1-methyl 2-hydroxyiminomethylpyridinium-1-methyl ether dichloride, dibromide or diiodide, a compound of claim 3.

10. 3-Cyclohexylcarbonylpyridinium-1-methyl 2-hydroxyiminomethylpyridinium-1-methyl ether dichloride, dibromide or diiodide, a compound of claim 6.

11. A pharmaceutical composition comprising, in admixture with a pharmaceutically-acceptable carrier an antidotal amount of a compound of claim 6 effective to prophylactically or therapeutically treat intoxication in a person or animal produced by a phosphorouscontaining cholinesterase inhibitor.

12. A prophylactic or therapeutic method of treating a person or animal for intoxication with a phosphorus-containing cholinesterase inhibitor, comprising administering to the person or animal a compound of claim 6 in an amount effective as an antidote for the cholinesterase inhibitor and in admixture with a pharmaceutically-acceptable carrier.

13. The method of claim 12, including a preliminary step of administering atropine.

14. The method of claim 12, wherein the effective amount is 0.2–40 mg./kg. of body weight.

15. A compound of claim 6 wherein R is in the 3- or 4-position.

16. A compound of claim 15 wherein R[1] is alkyl of 1–4 carbon atoms, cyclohexyl, phenyl, alkylphenyl of 1–4 carbon atoms in the alkyl, methoxyphenyl, dichlorophenyl or benzyl.

17. A compound of claim 1 wherein —CO—NR[2]R[3] is in the 3- or 4-position.

* * * * *